US00PP31519P2

(12) United States Plant Patent
Kleinwee

(10) Patent No.: US PP31,519 P2
(45) Date of Patent: Mar. 3, 2020

(54) ***LOBELIA* PLANT NAMED 'LOBZ0018'**

(50) Latin Name: *Lobelia erinus*
Varietal Denomination: LOBZ0018

(71) Applicant: SYNGENTA CROP PROTECTION AG, Basel (CH)

(72) Inventor: Theodorus Cornelis Maria van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,331

(22) Filed: Mar. 27, 2019

(51) Int. Cl.
*A01H 5/02* (2018.01)
*A01H 6/26* (2018.01)

(52) U.S. Cl.
USPC ..... Plt./451
CPC ..... *A01H 6/26* (2018.05)

(58) Field of Classification Search
USPC ..... Plt./451
CPC ..... A01H 5/02
See application file for complete search history.

*Primary Examiner* — Kent L Bell
(74) *Attorney, Agent, or Firm* — Dale Skalla

(57) ABSTRACT

A new *Lobelia* plant named 'LOBZ0018' particularly distinguished by its relatively large, light violet flowers, medium green foliage, very good branching and a semi-trailing to trailing plant habit.

1 Drawing Sheet

Latin name of the genus and species of the plant claimed: *Lobelia erinus.*

Varietal denomination: 'LOBZ0018'.

BACKGROUND OF THE NEW PLANT

The present invention comprises a new and distinct cultivar of *Lobelia*, botanically known as *Lobelia erinus* and hereinafter referred to by the cultivar name 'LOBZ0018'.

'LOBZ0018' is a product of a planned breeding program. The new cultivar has relatively large, light violet flowers, medium green foliage, very good branching and a semi-trailing to trailing plant habit.

The seed from which the variety was grown originates from an open pollination made on the open field in the summer of 2012, The Netherlands.

The female parent was a commercial *Lobelia* variety 'Blue Lagoon' (not patented), with a trialing plant habit, dark blue flower color and less vigorous than 'LOBZ0018'.

The male parent of 'LOBZ0018' is unknown, as the cross from which the variety originates was an open pollination.

The resulting seeds were sown in May 2013, and 'LOBZ0018' was selected as one flowering plant within the progeny of the stated cross in September 2013 in a controlled environment in Andijk, The Netherlands.

The first act of asexual reproduction of 'LOBZ0018' was accomplished when vegetative cuttings were propagated from, the initial selection in the fall of 2013 in a controlled environment in Andijk, The Netherlands.

BRIEF SUMMARY OF THE INVENTION

Horticultural examination of plants grown from cuttings of the plant initiated in the spring of 2014 in Andijk, The Netherlands, and continuing thereafter, has demonstrated that the combination of characteristics as herein disclosed for 'LOBZ0018' are firmly fixed and are retained through successive generations of asexual reproduction.

'LOBZ0018' has not been observed under all possible environmental conditions. The phenotype may vary significantly with variations in environment such as temperature, light intensity and day length.

A Plant Breeder's Right for this cultivar has not yet been applied for. 'LOBZ0018' has not been made publicly available prior to the effective filing date of this application, notwithstanding any disclosure that may have been made less than one year prior to the effective filing date of this application by the inventor or another who obtained 'LOBZ0018' directly from the inventor.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

Figure 1:
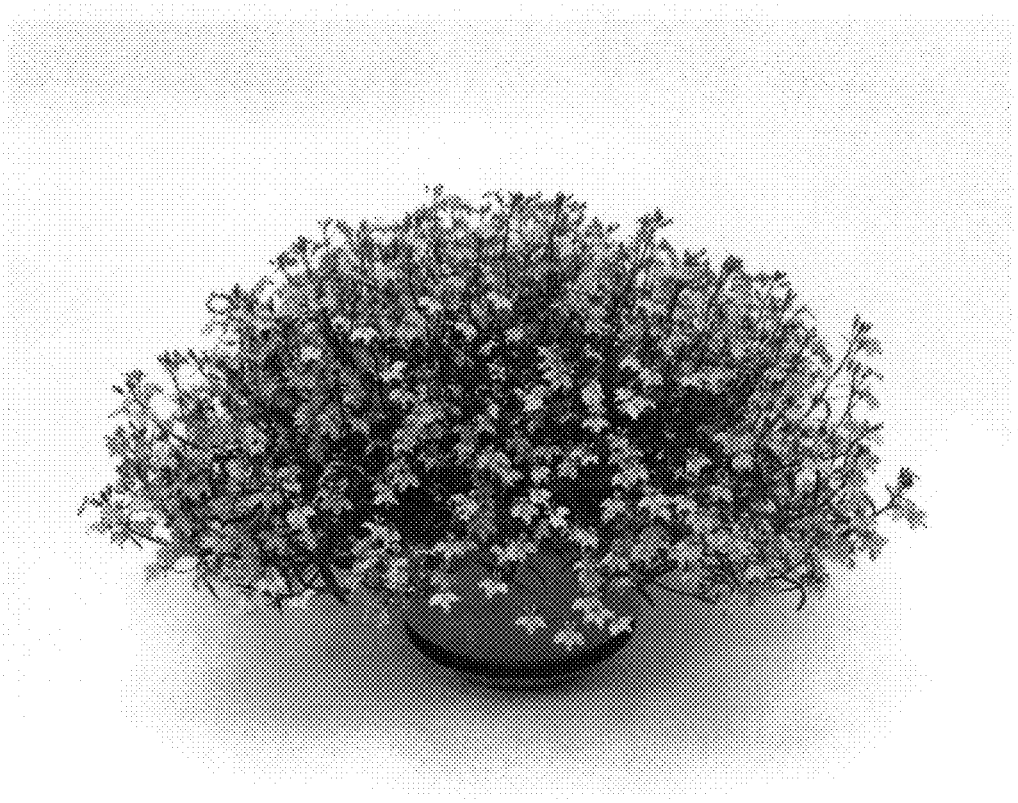
Figure 2:
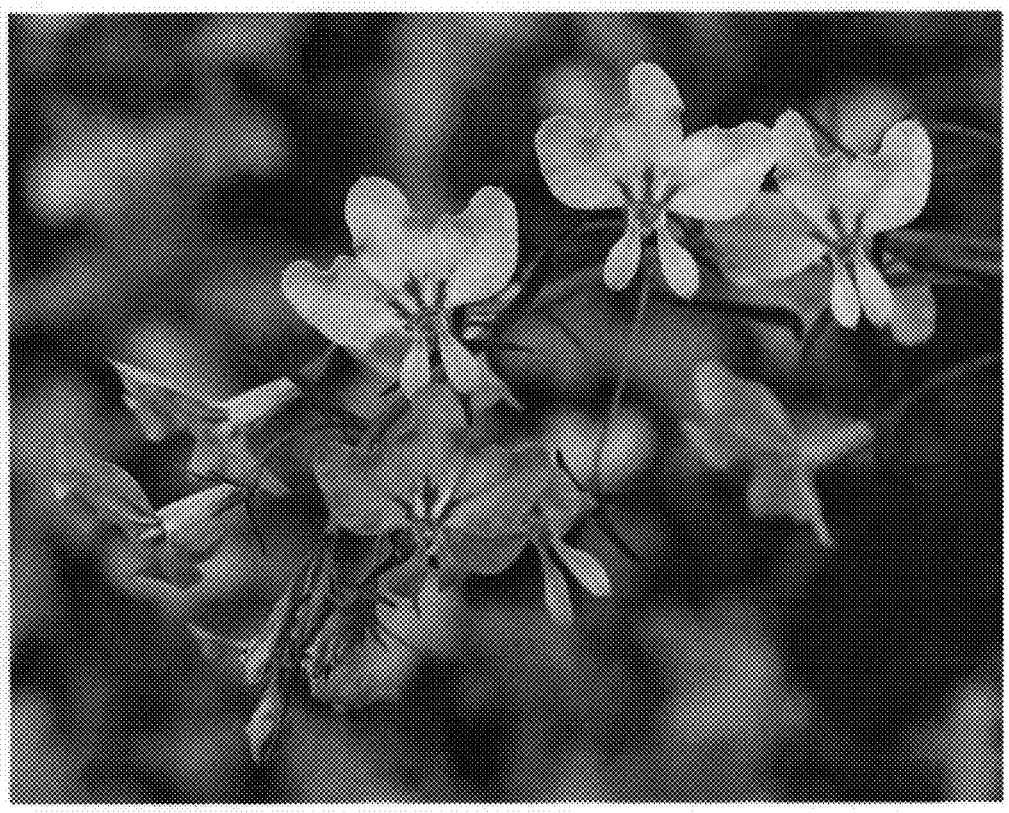

The accompanying photograph drawings show typical flower and foliage characteristics of 'LOBZ0018' with colors being as true as possible with an illustration of this type. The drawings show in FIG. 1 a flowering potted plant of the new variety and in FIG. 2 a close-up of its flowers.

DETAILED BOTANICAL DESCRIPTION

The aforementioned photographs were taken in April 2018 from plants grown in an indoor trial in Andijk, The Netherlands. These plants were grown in containers and were approximately 11 weeks of age. The close-up photograph was taken at the same time.

The measurements were taken in Andijk, The Netherlands in September 2018 on 17 week old plants that were grown outside in containers. Culture of these plants had started in week 21, 2018 with planting of rooted, non-pinched cuttings.

Color chart used: The Royal Horticultural Society Colour Chart (R.H.S.), 2001.

DIFFERENCES BETWEEN THE NEW VARIETY 'LOBZ0018' AND A MOST SIMILAR VARIETY

| | 'LOBZ0018' | 'LOBMOUNLILA', U.S. Plant Pat. No. 18,410 |
|---|---|---|
| Flower color: | Light violet | Darker violet to rose |
| Flower, diameter: | Relatively large | Relatively small |
| Plant habit: | Trailing to semi-trailing, rather vigorous | Trailing, vigorous |

Plant:

*Growth and habit*.—Rather vigorous; dense and freely branched with short internodes, mounding to semi trailing plant habit.

*Height*.—About 10 cm.

*Height* (*inflorescence included*).—22 cm.

*Width*.—45 cm.

*Branching characteristics*.—7 main stems, each with 3 to 4 secondary branches.

*Crop time to flowering, resp*.—Time to produce a finished flowering plant: About 12 weeks for a 12 cm pot.

*Garden performance*.—Used as patio planters, in mixed container plantings, or in garden beds.

*Time to initiate and develop roots*.—14-20 days at 22° C.

*Root description*.—Fibrous and freely branching.

Stem:

*Characteristics*.—With slightly strengthened, protruding edges, side branches are developed at almost every node.

*Stem length*.—Between 14-25 cm.

*Diameter*.—0.2-0.4 cm.

*Internode length*.—2.0-4.5 cm.

*Color*.—RHS 143A, 138A when older.

*Texture*.—Slightly pubescent.

Foliage:

*Arrangement*.—Alternate.

*Shape*.—Lanceolate.

*Apex*.—Acute.

*Base*.—Attenuate.

*Margin*.—Slightly incised.

*Leaf length*.—2.0-3.5 cm.

*Leaf width*.—0.2-0.9 cm.

*Immature leaf, color upper surface*.—RHS 143A.

*Immature leaf, color lower surface*.—RHS 143A.

*Mature color upper surface*.—RHS 137A.

*Mature color lower surface*.—RHS 138A.

*Venation type*.—Pinnate.

*Venation color, upper surface*.—RHS 143A.

*Venation color, lower surface*.—RHS 143A.

*Texture*.—Smooth to only occasionally a small hair.

*Petiole*.—No petiole, leaves are sessile.

Inflorescence:

*Type of inflorescence*.—Raceme, composed of single flowers in an alternate arrangement with one flower per node, subtended by a small leaflet.

*Blooming habit*.—Continuous through the growing season from spring to the fall.

*Quantity of inflorescences per plant*.—About 200.

*Quantity of flowers per inflorescence*.—Up to 1-2 open flowers.

*Lastingness of individual blooms on the plant*.—3-6 days, depending on temperature.

*Fragrance*.—None.

*Inflorescence length*.—Up to 5 cm.

Peducle:

*Color*.—RHS 138A.

*Length*.—Up to 15 cm.

*Diameter*.—0.2 cm.

*Texture*.—Pubescent.

Pedicels:

*Color*.—RHS 137B.

*Length*.—1.6-2.0 cm.

*Diameter*.—0.1 cm.

*Texture*.—Smooth, only occasionally a small hair.

Flower:

*Corolla type and shape*.—Single, zygomorphic; upper lip is formed by two small petals, lower lip has three larger petals; petals are fused at the base forming a relatively long funnel-shaped tube.

Immature flower:

*Main color upper surface*.—RHS 81B and at base RHS 81A.

*Main color lower surface*.—RHS 81C to RHS 81D.

*Immature flower, width*.—1.6 cm.

Mature flower:

*Flower*, (*horizontal*) *length*.—2.0 cm.

*Flower*, (*horizontal*) *width*.—2.0 cm.

*Flower, vertical length* (*depth*).—1.5 cm.

*Color upper lip, upper surface*.—RHS 81B.

*Color upper lip, lower surface*.—RHS 81D.

*Upper petal lobes, length* (*from the tube opening*).—1 cm.

*Upper petal lobes, width*.—0.3 cm.

*Color lower lip, upper surface*.—RHS 81B, fading RHS 81C when old.

*Color lower lip, lower surface*.—RHS 81D.

*Nectaries at base of lower petals*.—RHS 155A.

*Lower petal lobes, length* (*from the corolla opening*).—1.3 cm.

*Lower petal lobes, width*.—0.8 cm.

*Tube, color* (*outside*).—RHS 81B.

*Tube length*.—0.9-1 cm.

*Tube width*.—0.3 cm.

Petal (lobes):

*Shape*.—Obovate.

*Apex*.—Mucronulate.

*Base*.—Fused.

*Margin*.—Entire.

*Texture upper surface*.—Glabrous, some pubescence near vein.

*Texture lower surface*.—Smooth.

Flower bud:

*Shape*.—Gibbous.

*Length*.—0.6 cm.

*Diameter*.—0.4 cm.

*Color* (*at tight bud*).—Part is RHS 81B to RHS 81C.

Calyx:

*Shape*.—5 sepals in a whorl, slanting outwards, bases fused.

*Sepal color*.—RHS 187A, very dark.

*Sepal length*.—0.9 cm.

*Width*.—0.1-0.2 cm.

*Shape*.—Ligulate.

*Apex*.—Acute.

*Base*.—Fused.

*Texture*.—Smooth.

Reproductive organs:
Stamens:
*Quantity.*—5.
*Filament, color.*—RHS N81C.
*Filament length.*—0.6 cm.
*Filament, diameter.*—0.1 cm.
*Anther color.*—RHS 189C.
*Anther length.*—0.2 cm.
*Pollen amount.*—Not observed.
Pistil:
*Quantity per flower.*—1.
*Length.*—0.7 cm.
*Stigma color.*—RHS 82A.
*Stigma length.*—0.2 cm.
*Style color.*—RHS 138D.
*Style length.*—0.6-0.8 cm.
Fruit and seed set: Yes, some seed development observed in the trial fields.
Disease and insect resistance: Resistance and susceptibility typical for the species, no special observations made.

What is claimed is:

1. A new and distinct cultivar of *Lobelia* plant named 'LOBZ0018' substantially as illustrated and described herein.

* * * * *